United States Patent [19]
Wang

[11] Patent Number: 5,869,693
[45] Date of Patent: Feb. 9, 1999

[54] BENZOCYCLOBUTENONES AND POLYMERS DERIVED THEREFROM

[75] Inventor: Zhi Yuan Wang, Ottawa, Canada

[73] Assignee: Carleton University, Ottawa, Canada

[21] Appl. No.: 855,761

[22] Filed: Apr. 24, 1997

Related U.S. Application Data

[63] Continuation of Ser. No. 576,410, Dec. 21, 1995, abandoned.
[51] Int. Cl.[6] .................... C07D 207/12; C07C 303/00; C07C 211/00; C07C 49/115
[52] U.S. Cl. .................... 548/544; 548/545; 548/546; 564/92; 564/428; 568/328
[58] Field of Search .................... 564/428, 92; 568/327; 548/544, 545, 546

[56] References Cited

PUBLICATIONS

CA:1993:147123, Zaky et al. Egypt J. Chem. (1991).
CA:1983:452963, Wasif et al. Bull.Soc.Chim.Belg(1983).
CA:1982:544054, Sorial et al. Int.J.Chem.Kinet(1982).
CA:1982:217417, Stevens et al. J. Org. Chem.(1982).

*Primary Examiner*—Peter D. Mulcahy
*Attorney, Agent, or Firm*—J. Wayne Anderson

[57] ABSTRACT

The invention disclosed relates to novel functionalized benzocyclobutenones of structural formula I

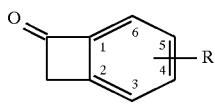

wherein R is $NH_2$, reactive $NH_2$ derivatives including acids, acid chlorides, amides and diazonium salts, OH, CN, $NO_2$, H, I, F Br, Cl, mercapto and deuterium. Also disclosed are polymer compositions comprising thermal reaction products of the benzocyclobutenones of formula I and either a polyol or a polyamine.

4 Claims, No Drawings

BENZOCYCLOBUTENONES AND POLYMERS DERIVED THEREFROM

This application is a Continuation of application Ser. No. 08/576,410, filed on Dec. 21, 1995, now abandoned.

BACKGROUND OF THE INVENTION

1. Field of the Invention

This invention relates to novel functionalized benzocyclobutenones (BCBOs) and to polymers derived therefrom.

A variety of modified polymers or toughened polymer blends can be produced in reactive processing such as molding, casting and melt blending, through the reactions of certain functional groups. For example, maleic anhydride-modified polyolefins or oxidized poly(phenylene oxide)s are reactive targets in these processes for covalent linkage with nylons. Acetylene may be introduced as a reactive end group into high-performance polymers such as NASA's LARC polyimides. It reacts to cause rapid crosslinking of the polymer at elevated temperatures without the evolution of volatiles during molding or melt processing.

2. Description of the Prior Art

In the late 1970s, Kirchhoff et al at the Dow Chemical Company initiated a research program on the use of benzocyclobutenes in polymer synthesis and modification. The first patent describing the use of benzocyclobutenes in the preparation of high molecular weight polymers was issued in 1985.[1] Similar work was independently by Tan and Arnold.[2] Since these initial discoveries, the field of benzocyclobutene polymers has rapidly expanded to include more than 50 patents and numerous papers.[3]

Benzocyclobutene can be viewed as a latent functional group that upon thermal activation can generate the highly reactive diene (o-quinodimethane), which can then enter into a wide variety of dimerization, oligomerization and Diels-Alder cycloaddition reactions. Thus, the basic technology based on benzocyclobutenes involves a family of thermally polymerizable monomers which contain one or more benzocyclobutene groups per molecule. Heating a bisbenzocyclobutene monomer without a dienophile (olefin or acetylene) leads to a highly crosslinked polymer. The AB monomer containing a benzocyclobutene and a vinyl group yields a linear Diels-Alder cycloaddition polymer upon thermolysis. The benzocyclobutene group is mainly used in a small amount as either an end group or a pendant group. Thus, it has been incorporated into high-performance polyimides, aromatic polyamide and poly(arylene ether)s. A variety of AB monomers have been synthesized and thermally cured to make polymers and composites for aerospace and electronic applications.

Although the benzocyclobutene chemistry is fascinating, the area of its application is confined due to its limited types of interpolymer coupling reactions (just dimerization and Diels-Alder cycloaddition). Accordingly, only dienes can be used as comonomers to produce linear thermoplastics. Other commercial materials such as diols and diamines could not be utilized, because of many unpredictable side reactions with the o-quinodimethane intermediate. In addition, the applications of this chemistry to vinyl polymers and polyols are scarce, as a few reports on the modification of polystyrene have appeared.[4]

Benzocyclobutenone (BCBO), similar to but different from benzocyclobutene, can be prepared in several ways.[5] Some substituted analogues, including 3-methyl-, 3-methoxy-, 4-methyl-, 4-methoxy-, 5-methyl-, 5-methoxy-, 6-methyl-, 4,4-dimethyl-, 3,6-dimethyl-, 3,6-dimethoxy, 3-methoxy-6-methyl-, 3-methyl-6-methoxy-, 3,4,5-trimethyl-, 3,4,5,6-tetramethyl-, 3,6-dimethoxy-4,5-dimethylbenzocyclobutenones are known.[6]

Benzocyclobutenone is also known to undergo the reaction with methanol and cycloaddition reactions with aldehyde and dienophiles such as maleic anhydride and dimethyl fumarate upon flash photolysis.[6d,7]

An isocoumarin as a dimer of benzocyclobutenone is also isolated from the reaction of o-(trimethylsilylmethyl) benzoyl chloride with cesium fluoride in refluxing acetonitrile.[7]

SUMMARY OF THE INVENTION

According to one aspect of the invention, novel functionalized benzocyclobutenone compounds of structural formula I are provided

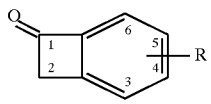

wherein R is $NH_2$, reactive $NH_2$ derivatives including acids, acid chlorides, amides, and diazonium salts, OH, CN, $NO_2$, H, I, F, Br, mercapto and deuterium.

According to another aspect of the invention, a polyfunctionalized compound of structural formula IA

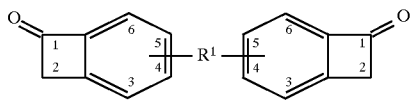

wherein R' is a polyvalent organic bridging group.

According to yet another aspect of the invention, a polymer composition comprising the thermal reaction product of a functionalized benzocyclobutenone compound of structural formula I as defined above, and a compound selected from a polyol and a polyamine, is provided.

According to a further aspect of the invention, a polymer composition comprising the thermal reaction product of a vinyl monomer containing a functionalized benzocyclobutenone of structural formula I as defined above, and a vinyl monomer, is also provided.

According to yet a further aspect of the invention, a novel process for the preparation of a thermally stable lactone or isocoumarin of structural formula III

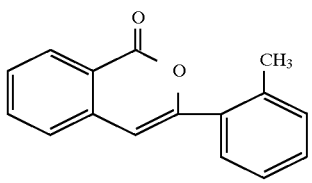

is provided comprising reacting a compound of structural formula IB

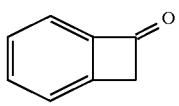

at a temperature of 150° to 300° C., preferably about 250° C.

According to yet another aspect of the invention, a novel process for the preparation of an o-methyl benzoate of structural formula IV

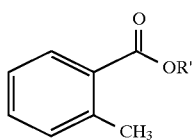  IV is provided which comprises reacting a compound of structural formula IB

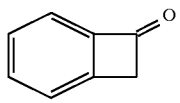  IB with an aliphatic or aromatic alcohol of formula

R'—OH wherein R' is alkyl, aryl or alkyl-substituted aryl, at a temperature of 150°–220° C.

According to a further aspect of the invention, a novel process for the preparation of a bis-o-methyl benzoate of structural formula V

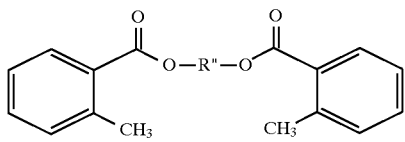  V is provided which comprises reacting a compound of structural formula IB

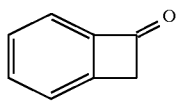  IB with a diol of formula

HO—R"—OH wherein R" is alkyl, aryl or alkyl-substituted aryl, at a temperature of 150°–220° C.

DETAILED DESCRIPTION OF THE INVENTION

Recently, we have demonstrated that benzocyclobutenone undergoes ring-opening at elevated temperatures. It is believed that a reactive vinyl ketene intermediate is formed which then reacts very rapidly by itself (dimerization) or with alcohols. Some model reactions are presented herein.

Reaction 1 (Scheme 1) demonstrates that dimerization occurs readily at 150° to 300° C., preferably about 250° C., to produce a thermally stable lactone or isocoumarin along with some oligomers.

Scheme 1

Model Reaction I: Dimerization and Oligomerization

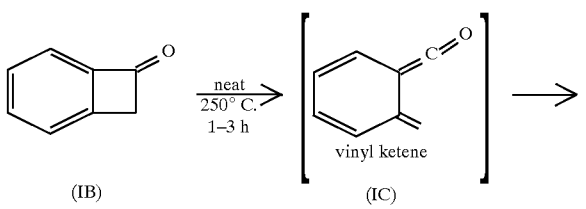

-continued
Scheme 1

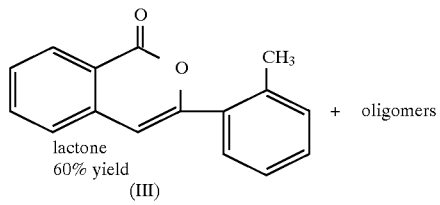

lactone
60% yield
(III)

Model reactions 2A and 2B show that the esters are readily formed in quantitative yields by heating a stoichiometric mixture of benzocyclobutenone and alcohols or diols, respectively, at relatively lower temperatures (150°–220° C.). In reaction 2A, heating benzocyclobutenone is believed to generate a reactive vinyl ketene which then couples with aliphatic (primary and secondary) and aromatic alcohols to give the corresponding o-methylbenzoates. In reaction 2B, aliphatic and aromatic diols of low or high molecular weights react with benzocyclobutenone, yielding bis-o-methylbenzoates in 100% yield.

Scheme 2

Model Reaction 2A and 2B.
Thermal Coupling With Alcohols and Diols, respectively

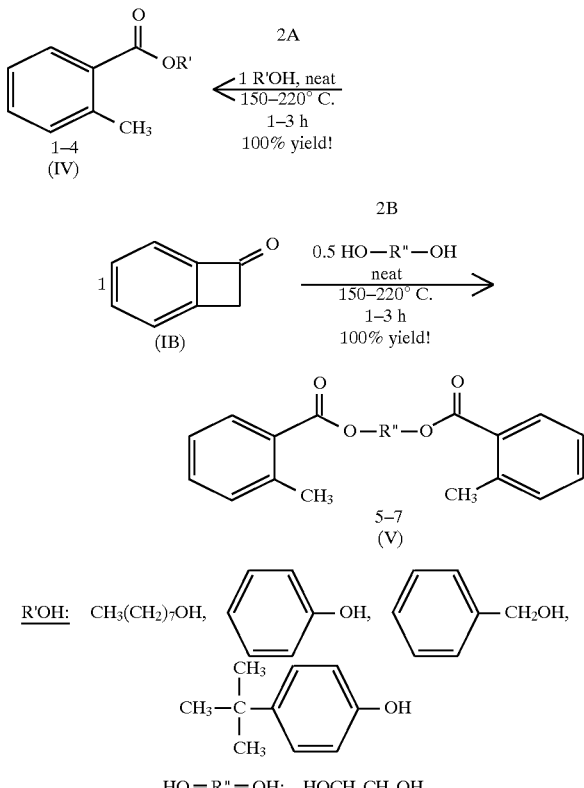

The unique feature of this BCBO chemistry is that thermal ring-opening/coupling reaction proceeds in high yield with no volatile by-products being produced. Therefore, this reaction is applicable for reactive processing such as casting, molding, and coating.

These reaction mechanisms can also be applied to thermal bulk polycondensation. As shown in Scheme 3, a difunctional BCBO derived from adipic acid was heated at 220°–240° C. together with a stoichiometric amount of a polyol and bisphenol A, respectively. Upon melting, the melt mixture quickly became viscous, indicating the polymer formation. As expected, the polymer containing a flexible oxyethylene block was elastomeric and the polymer derived from semi-rigid bisphenol A appeared to be hard.

Simply heating 5-aminobenzocyclobutenone (8) in neat or in high boiling solvents such as aromatic halogenated hydrocarbons and aromatic ethers e.g. o-dichlorobenzene, 1-chloronaphthalene and diphenylether, at 180°–210° C. led to the formation of the corresponding aromatic polyamide. Spectroscopic data were consistent with the structures of these polymers.

Scheme 3

Model Bulk Polycondensation

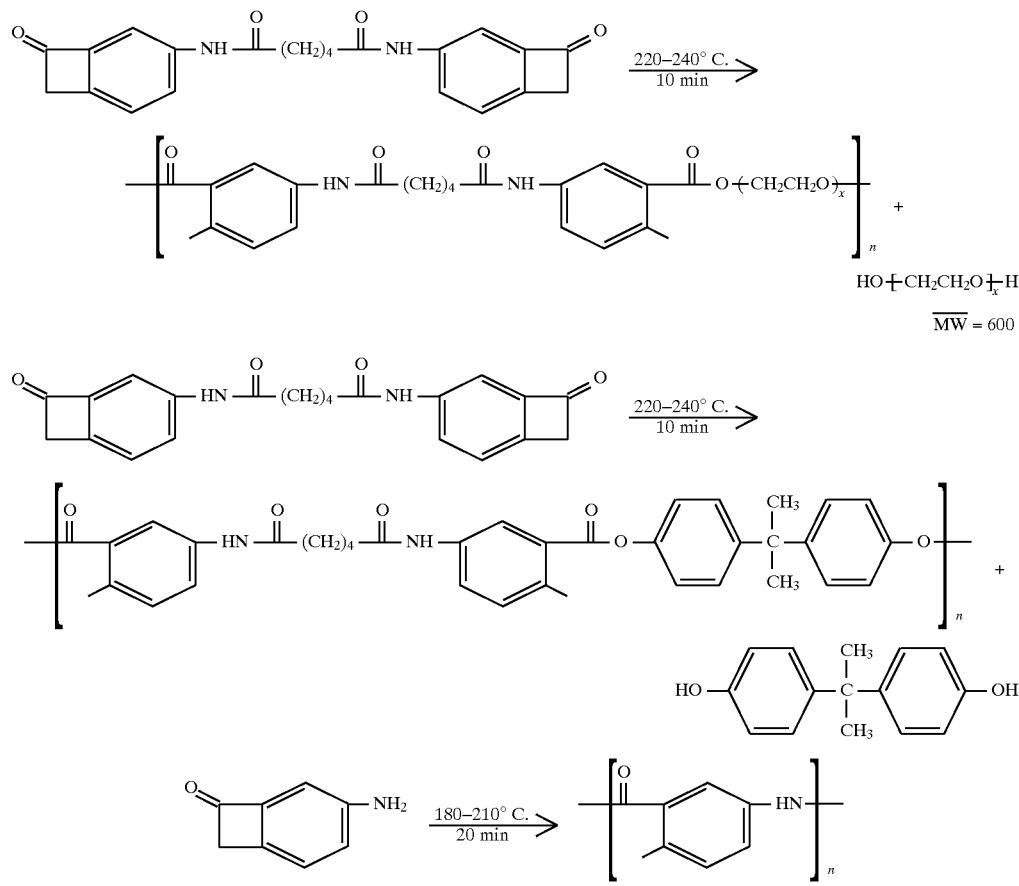

BCBOs can be easily produced in large scale from inexpensive anthralic acid or 2-toluic acid.[5] A hundred-gram scale synthesis has performed in our laboratory, offering a possibility for having a cost-effective approach.

Some novel functional BCBO derivatives, illustrated below, have been prepared in our laboratory and show a range of the onset cure temperatures (Tc=200°–300° C.).

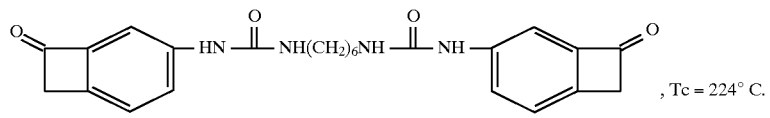

, Tc = 224° C.

13

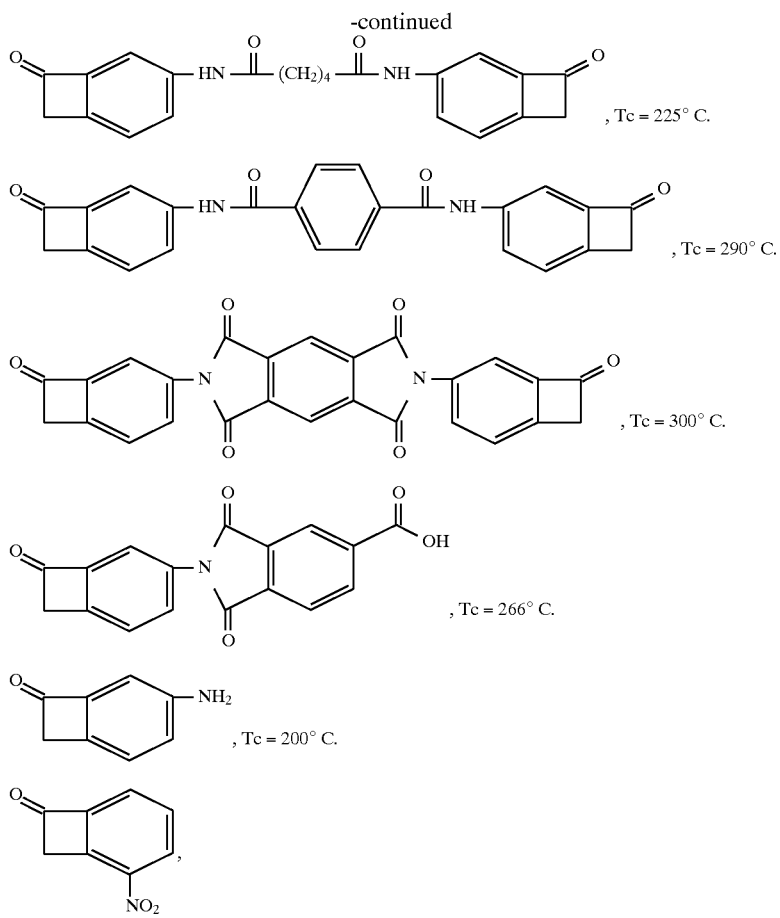

Compounds 8,9 and 15–20 represent mono-functional derviatives and compounds 10–13 represent di-functional derivatives. The di-functional compounds include two unfunctionalized BCBO structures in which the benzo part of the structures are connected by a polyvalent organic bridging group. Examples of polyvalent bridging groups can be found in U.S. Pat. No. 4,540,763 at column 4, begining at line 20, the disclosure of which is incorporated herein by reference.

5-Aminobenzocyclobutenone(8) is prepared by reduction of 5-nitrobenzocyclobutenone. It is an important starting material to introduce reactive benzocyclobutenone moiety in common commodity polymers, such as polystyrene, polyacrylates, and epoxy resins, and high-performance polymers like poly(ether ketone)s and poly(ether sulfone)s.

The formation of compounds 9–12 demonstrates that BCBO can be introduced as an endgroup into a wide spectrum of polymers containing carboxylic acid or its derivatives (e.g., acid chloride and anhydride). Examples of these polymers include nylons, polyesters, polyimides, and their copolymers. The formation of compound 13 shows that 5-aminobenzocyclobutenone itself can be incorporated at the ends of the isocyanate-based resins such as polyurethanes and their copolymers.

The trifunctional compound 14 can be used for cross-linking polyols or hydroxy-terminated oligomers. Compound 15 containing a fluorine group should be reactive towards a nucleophile in nucleophilic displacement polycondensation with a variety of bisphenols. Thus, BCBO can be introduced, via compound 15 or its analogues, at the ends of poly(arylene ether ketone)s and poly(arylene ether sulfone)s.

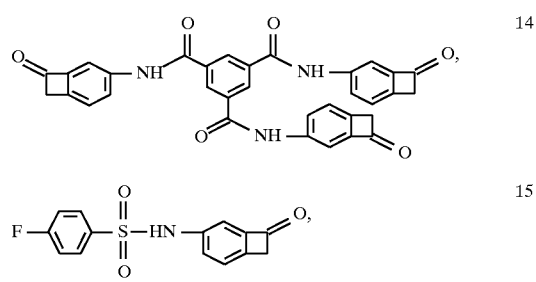

Furthermore, a variety of end-capped polymers can be subjected to curing with or without a diol/polyol. It can be expected that either with or without a polyol during curing, a cross-linked resin will be obtained. The degree of cross-linking can be easily controlled with the amount of the BCBO unit introduced in the polymer. With a diol, chain extension can be effected. Similarly, curing an oligomeric diol together with a BCBO end-capped prepolymer should produce a new block copolymer. As many hydroxy-terminated polymers are commercially available and a variety of commercial polymers can be end-capped with BCBO, the numbers of new block copolymers that can be made based on this BCBO are enormous.

Diazotization of 5-aminobenzocyclobutenone gives a versatile diazonium salt intermediate which is then transformed to compounds 16 and 17 by conventional replacement reactions. Compound 16 can be used as an end-capping agent for many aliphatic and aromatic polyesters. According well-established chemistry of diazonium salts, other benzocyclobutenones having fluoro, chloro, bromo, cyano, mercapto, azido and deuterium groups can be prepared.[8]

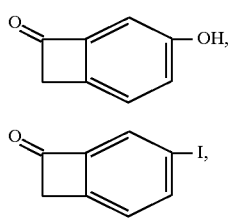

Vinyl polymers are derived from vinyl monomers such as ethylene, styrene, methacrylates, and maleic anhydride. Introducing a reactive benzocyclobutenone into vinyl polymers would allow further manipulation of the polymer structure (e.g., grafting, branching or crosslinking) during processing. The most convenient way to introduce this reactive group is by copolymerizations of BCBO-containing vinyl monomers with commercial vinyl monomers such as styrene and (meth)acrylates. Two such monomers 18 and 19 have been prepared from 5-aminobenzocyclobutenone(8) which is derived from benzocyclobutenone by simple nitration and subsequent reduction in high yields. Free-radical bulk copolymerization of two different monomers in certain ratios would be the choice of polymerization-methods, since it is still the most economical process to manufacture polystyrene and many other vinyl polymers. Preliminary thermal studies have shown that 18 and 19 are stable to about 300° C. before ring opening occurs. Therefore, post-polymerization (or curing) can be carried out during melt processing above 300° C.

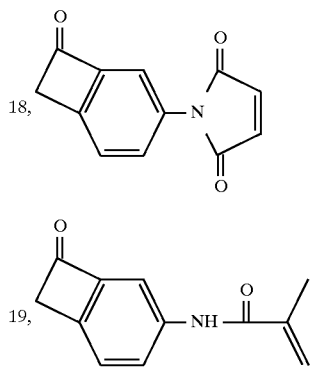

Finally, 3-nitrobenzocyclobutenone (20) synthesized herein can be reduced as its isomer to form 3-aminobenzocyclobutenone. Thus, starting from 3-nitrobenzocyclobutenone, the corresponding isomers of all compounds (ca. 9–19) which are derived from 5-aminobenzocyclobutenone can be made available.

EXAMPLES

General Methods and Instrumentation

Melting points were taken on a Fisher-Johns melting apparatus and are uncorrected or from DSC. $^1$H and $^{13}$C NMR spectra were recorded on either a Varian Gemini-200 or a Bruker-400 instrument using tetramethylsilane as an internal reference. The following abbreviations are used to describe peak patterns when appropriate: s=singlet, d=doublet, t=triplet, q=quartet, m=multiplet, and br=broad. Infrared measurements were performed on a Perkin Elmer 1600 FTIR instrument. Low resolution mass spectra were obtained on a Du Pont 21-492B instrument. Glass transition temperatures and onset temperatures for extermic ring-opening were obtained using differential scanning calorimetry (DSC) on a Seiko DSC 220 at a heating rate of 10° C. per min under nitrogen.

Materials 4,4'-Isopropylidenediphenol (BPA), phenol, benzyl alcohol, 4-t-butylphenol, ethylene glycol, polyethylene glycol, terephthalyol dichloride, maleic anhydride, pyromellitic dianhydride, trimellitic anhydride, methacryloyl chloride, 4-fluorobenzenesulfonyl chloride, 1,3,5-benzenetricarbonyl trichloride, 1,6-hexamethylenediisocyanate, N,N,-dimethylformamide, N,N-dimethylacetamide (DMAc), N-methyl-2-pyrrolidinone (NMP), thionyl chloride, and other common organic solvents were purchased from Aldrich Chemical Co., Milwaukee, Wis., U.S.A. and used as received. Benzocyclobutenone was prepared from anthranilic acid according to literature procedure.[5c]

Example 1

Thermolysis of Benzocyclobutenone

Benzocyclobutenone (0.556 g) was placed in the sealed tube and heated at 180°–190° C. for 1 hour, 200°–210° C. for 1.5 hours, and then 230°–240° C. for 1.5 hours. The resulting dark viscous liquid was cooled to room temperature and poured into methanol. The methanol solution was filtered and the filtrate was concentrated. The residue was purified by chromatography. A compound was isolated and identified as the isocoumarin: 0.290 g (52%); mp 84°–85° C. (lit.[7] mp 63°–65° C.); IR and NMR spectra were consistent with the reported ones;[7] MS (EI, m/e, relative intensity %) 236 (M+., 31), 208 (M+.–CO, 24).

Example 2

Reactions of Benzocyclobutenone with Alcohols

A general procedure is as follows: Benzocyclobutenone and an alcohol were placed in the sealed tube and heated in an oil bath at 150°–220° C. for 4–30 hours. The product was purified by chromatography, if necessary. The ratio of reactants, reaction temperature and time, and yield are summarized in Table 1.

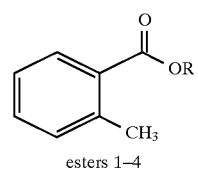

esters 1–4

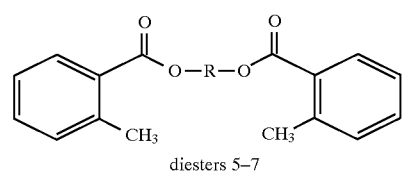

diesters 5–7

Reactions of benzocyclobutenone with alcohols.

| Product | R | Alcohol | Amount (meq)[a] | Temp. (°C.) | Time (h) | Yield[b] (%) |
|---|---|---|---|---|---|---|
| 1 | —(CH$_2$)$_7$CH$_3$ | 1-octanol | 4.0 | 220 | 21 | 94.0 |
|   |   | 1-octanol | 1.25 | 215 | 30 | 79.3 |
| 2 | Ph- | PhOH | 1.05 | 150 | 8 | 39.1 |
|   |   | with DABCO | 1.05 | 190 | 4 | 39 |
| 3 | PhCH$_2$— | PhCH$_2$OH | 1.13 | 160 | 6 | 44 |
| 4 | p-t-BuPh- | p-t-BuPhOH | 1.02 | 200 | 2 | 100 |
| 5 | —CH$_2$CH$_2$— | HOCH$_2$CH$_2$OH | 0.5 | 200 | 18 | 100[c] |
| 6 | -PhC(CH$_3$)$_2$Ph- | Bisphenol A | 0.44 | 200 | 2 | 100 | a, molar equivalent to benzocyclobutenone used. b, isolated yield. c, a mixture of monomeric and dimeric esters with a ratio of 1.0 to 1.3.

Example 3
Formation of the Polymer 7 with Polyethylene Glycol

Polyethylene glycol with average molecular weight of 600 (0.48 mmol) was heated together with 1 mmol of benzocyclobutenone at 190° C. for 18 hours. The polymer 7 with o-methylbenzoate end groups was obtained in 100% yield. IR shows the characteristic carbonyl band at 1715 cm$^{-1}$ for the ester group.

Example 4
5-Nitrobenzocyclobutenone

Benzocyclobutenone (3.0 g, 25.42 mmol) was added slowly to concentrated sulfuric acid (6 mL) at −5° C.–0° C. with vigorous stirring. The resulting solution was further cooled to −10° C. and the mixture of concentrated sulfuric acid (3 mL) and nitric acid (70%, d 1.42, 2.0 mL) was added at such a rate that the solution temperature remained between −10° C. and −5° C. After the completion of addition of nitrating solution, stirring continued for 10 min. The reaction mixture was then poured into an ice slurry (30 g of ice in 30 mL of water). The product which precipitated out as yellow solids from water was collected by suction filtration and washed with water twice, aqueous sodium carbonate solution (10%) twice, and water twice consecutively. The solid product was recrystallized from methanol to give white fine crystals: 3.44 g (83.1%); mp 126°–127° C.; IR (KBr) 1342, 1522, 1785 cm$^{-1}$; 1H NMR (200 MHz, CDCl3) 4.16 (s, 2H), 7.95 (d, 1H), 8.22 (s, 1H), 8.51 (d, 1H); MS (EI, m/e, relative intensity %) 163 (M+., 99.3), 135 (M+. −CO, 39.3), 89 (135 −.NO2, 100).

Example 5
5-Aminobenzocyclobutenone (8)

In a 100 mL two-neck round-bottomed flask fitted with a reflux condenser, were placed 5-nitrobenzocyclobutenone (2.50 g, 15.34 mmol), iron powder (2.50 g) and aqueous ethanol (50%, 25 mL). The mixture was heated to gentle boiling. With a good stirring, concentrated hydrochloric acid (36%, 0.15 mL) in aqueous ethanol (50%, 5 mL) was added slowly. Stirring and reflux stopped until TLC showed no more starting compound. It usually took 5–60 min. After cooling to room temperature, the reaction solution was treated with sodium carbonate powders to pH 8–9. The insoluble solids were removed by filtration and further washed with methanol. The filtrate and washing solution were combined and concentrated by distillation at 50° C. under vacuum. Upon cooling, the pure product crystallized out and then collected by suction filtration: 1.88 g (92.4%); mp 92°–93° C.; IR (KBr) 1620, 1744, 3362, 3466 cm$^{-1}$; 1H NMR (200 MHz, CDCl3) 3.85 (s, 2H), 3.86 (s, 2H), 6.64 (s, 1H), 6.88 (d, 1H), 7.33 (d, 1H); MS (EI, m/e, relative intensity %) 133 (M+., 31.2), 105 (M+. −CO, 100).

Example 6
Acid Compound 9 from Reaction of 8 with Trimellitic Anhydride

A mixture of 8 (665 mg, 5.0 mmol) and trimellitic anhydride (960 mg, 5.0 mmol) in dimethylacetamide (10 mL) was heated at 160° C. for 2 hours. After cooling to room temperature, the solid 9 was collected on the filter funnel, washed with diethyl ether and dried in air. Yield: 1.35 g (88%); IR (KBr) 1725, 1774, 3500 cm$^{-1}$. DSC scan showed a melting endotherm at 115° C. and two exotherms peaked at 266° and 284° C.

Example 7
Transformation of the Acid 9 to the Acid Chloride

The acid 9 in example 6 (0.5 g) was stirred in thionyl chloride (5 mL) at 80° C. for 90 minutes. After cooling to room temperature, the acid chloride product as solid was filtered and washed with hexane. The product was pure enough for further reactions without recrystallization from toluene. Yield: 0.55 g (100%); IR (KBr) 1724, 1783, 1790 cm$^{-1}$; 1H NMR (200 MHz, CDCl3) 4.05 (s, 2H), 7.45 (s, 1H), 7.60 (d, 1H), 7.70 (d, 1H), 8.12 (d, 1H), 8.56 (d, 1H), 8.69 (s, 1H); MS (EI, m/e, relative intensity %) 327 (M+. +2, 26.4), 325 (M+., 79.3), 297 (M+. −CO, 100).

Example 8
Compound 10 from Reaction of 8 with Pyromellitic Dianhydride

The mixture of 8 (0.40 g, 3.01 mmol) and pyromellitic dianhydride (0. 312 g, 1.432 mmol) in dimethylacetamide (6 mL) was gradually heated up to reflux (160° C.). At 100° C., the intermediate amic acid was formed and precipitated out. It redissolved at 160° C. After 15–20 minutes, yellow precipitates formed again, indicating the formation of the diimide product. The reaction continued for another 60 minutes and cooled to room temperature. Ethanol (5 mL) was added and the product was collected by suction filtration. After washing with ethanol and drying in a vacuum oven at 80° C. overnight, the product 10 was obtained as yellow powders: 0.41 g (64%); IR (KBr) 1724, 1783 cm$^{-1}$. It is insoluble in many organic solvents such as ethanol, chloroform, toluene, dimethylformamide, dimethylacetamide and N-methylpyrrodilinone and displays no melting point before ring-opening. DSC showed an exotherm at 300° C. in the first scan, indicating the ring-opening of benzocyclobutenone unit. Second DSC scan displayed no peaks up to 450° C.

Example 9
Compound 11 from Reaction of 8 with Terephthaloyl Dichloride

To a suspension of 8 (0.40 g, 3.01 mmol) and sodium hydroxide (0.48 g) in water (5 mL), were added terephthaloyl dichloride (0.29 g) in THF (3 mL). The flask was covered with a cock and shaken vigorously for 10–15 minutes. The resulting white to pale yellow solids were collected on the filter funnel and washed with water (10 mL) and 95% ethanol (10 mL) and dried in air. Yield was 0.27 g (45%); IR (KBr) 1656, 1751 cm$^{-1}$. Recrystallization was done using dimethylformamide. No melting was observed below 300° C. DSC up to 450° C. showed an exotherm at 290° C. in the first scan, indicating the ring-opening of benzocyclobutenone unit. Second DSC scan displayed no peaks up to 450° C.

Example 10
Compound 12 from Reaction of 8 with Adipoyl Chloride

At room temperature, to a solution of 8 (1.45 g) in 5 mL of dry pyridine, was added of sodium nitrate (0.759 g) in 5 mL of water was added adipoyl chloride (1.0 g) dropwise under nitrogen. After stirring for one hour, the resulting red-orange slurry was poured into water (200 mL). The resultant solids were washed with water (2×200 mL) and methanol (2×50 mL). After drying at 60° C. in a vacuum oven, the pure product 12 was obtained as a yellow solid: 1.67 g (81.5%); mp 222° C.; IR (KBr) 1743, 1677 cm$^{-1}$; 1H NMR (400 MHz, DMSO-d6) 1.65 (m, 4H), 2.37 (m, 4H), 7.58 (d, 2H), 7.67 (d, 2H), 8.56 (d, 2H), 7.75 (s, 2H), 10.14 (s, 2H, N-H); MS (EI, m/e, relative intensity %) 376 (M+., 10.8), 348 (M+. –CO, 22.1). DSC scan showed a melting endotherm at 222° C. and a exotherm starting at 225° C. and peaked at 272° C.

Example 11
Compound 13 from Reaction 8 with 1,6-Hexamethylenediisocyanate

The solution of 5-aminobenzocyclobutenone (8) (0.30 g) and hexamethylenediisocyanate (0.20 g) in dry THF (5 mL) was refluxed for 2 hours. After cooling to room temperature, some precipitates formed and were collected by filtration. Further washing with ether and drying in vacuo at 60° C. gave the product 13 as light yellow solids (0.26 g, 53.1%). mp 211.2° C.; IR (KBr) 1623, 1763, 2860, 3306 cm$^{-1}$; 1H NMR (200 MHz, DMSO-d6) 1.31 (m, 4H), 1.44 (br t, 4H), 2.50 (m, 4H), 3.87 (s), 6.20 (t, 2H, N-H), 7.44 (d d, 1H), 7.50 (d, 1H), 7.55 (s, 1H), 8.63 (s, 2H, ArN-H); 13C NMR (50 MHz, DMSO-d6) 31.61, 35.16, 56.54, 113.57, 129.59, 131.08, 147.06, 149.16, 153.13, 160.57, 193.70; MS (EI, m/e, relative intensity %) 301 (M+. –133, 0.5), 159 (76.6), 131 (159 –CO, 100). DSC showed a melting endotherm peaked at 211.2° C. and an exotherm beginning at 224.0° C. with two peaks at 226.2° C. and 265.3° C. in the first scan. The second scan displayed no peaks up to 350° C.

Example 12
Bulk Polycondensation of 12 and Polyethylene Glycol

The mixture of 12 (0.125 g) and polyethylene glycol (MW=600, 0.201 g) in a flask was heated to 220°–240° C. (oil bath temperatures) under nitrogen. The liquid became viscous rapidly. The reaction was over in 15 minutes. The polymer product appeared elastomeric and was soluble in chloroform, dimethylformamide, dimethylacetamide, and 1,1,2,2-tetrachloroethane but not in DMSO. IR displayed the typical carbonyl bands at 1718 cm$^{-1}$ for the ester and at 1678 cm$^{-1}$ for the amide.

Example 13
Bulk Polycondensation of 12 and Bisphenol A

The mixed solids of 12 (0.253 g) and bisphenol A (0.152 g) in a flask were heated to 200° C. (oil bath temperatures) under nitrogen. The solids melted and soon solidified. After increasing the temperature to 240° C., a viscous melt was formed in less than 5 minutes. After 20 minutes at 240° C., the polymer was obtained as a hard solid which was soluble in DMSO but not in chloroform and 1,1,2,2-tetrachloroethane. A fiber or a film can be made directly from the polymer melt. IR displayed the typical carbonyl bands at 1739 cm$^{-1}$ for the ester and at 1662 cm$^{-1}$ for the amide. The glass transition was found to be 157° C. by DSC.

Example 14
Thermal Polymerization of 5-Aminobenzocyclobuteneone (8)

A sample vial containing solid 5-aminobenzocyclobuteneone (8) was heated in an oil bath at 180°–210° C. for 20 minutes. IR of the resulting resin displayed a new peak at 1676 cm due to the amide group and very weak peak due to unreacted ketone. DSC of the cured resin showed a weak transition near 190° C.

Example 15
Compound 14 from Reaction of 5-Aminobenzocyclobutenone (8) with 1,3,5-Benzenetricarbonyl Trichloride The mixture of 5-aminobenzocyclobutenone (0.93 g) and with 1,3,5-benzenetricarbonyl trichloride (0.50 g) in dry pyridine (10 mL) and DMSO (2 mL) was heated at 70° C. for 18 hours. The clear solution was poured into water to give yellow precipitates. The solids were collected by filtration and washed with water and methanol. After drying at 50° C. under vacuum, the pure triamide 14 was obtained (0.89 g, 85%). IR (KBr) 1680 (amide), 1758 (C=O), 3312 (NH) cm$^{-1}$; 1H NMR (200 MHz, DMSO-d6) 4.01 (s, 6H), 7.74 (br s, 3H), 7.95 (br s, 6H), 8.75 (s, 3H, N-H); MS (EI, m/e, relative intensity %) 301 (M+. –133, 0.5), 159 (76.6), 131 (159 –CO, 100). DSC showed no melting endotherm, except for an exotherm beginning at 283.9° C. and peaked at 290.8° C. in the first scan. The second scan displayed no peaks up to 350° C.

Example 16
Compound 15 from Reaction of 5-Aminobenzocyclobutenone (8) with 4-Fluorobenzenesulfonyl Chloride The amine 8 (0.33 g) in dry pyridine (2 mL) at room temperature with stirring. 4-Fluorobenzenesulfonyl chloride (0.5 g) was added in one portion. Stirring continued overnight. The red solution was poured into water (10 mL). To this suspension, methanol was then added until a clear solution was formed. On standing at room temperature overnight, the product was crystallized out. After filtration, washing with aqueous methanol (30% by volume) twice and drying in vacuo, the product 15 was obtained in 98% yield (70.8 g). mp 146.1° C. (DSC); IR (KBr) 1162, 1759, 3243 cm$^{-1}$; 1H NMR (200 MHz, CDCl3) 3.92 (s, 2H), 7.14 (br t, 2H, o-F-ph-H), 7.29 (d d, 1H), 7.35 (br s, 1H, NH), 7.45 (d d, 1H), 7.81 (m, 2H); MS (EI, m/e, relative intensity %) 291 (M+., 27), 263 (M+. –CO, 39), 132 (263 (M+. –.SO2Ph, 39), 104 (133 –CO, 100). DSC showed a melting endotherm peaked at 146.1° C. and an exotherm beginning at 210.6° C. and peaked at 222.0° C. in the first scan. The second scan displayed no peaks up to 350° C.

Example 17
5-Hydroxybenzocyclobutenone (16)

To a cold solution of phosphoric acid (75%, 1.788 g), were added 5-aminobenzocyclobutenone (0.502 g), sulfuric acid (0.20 g) and water (10 mL). The solution of sodium nitrite (0.196 g) in water (1 mL) was then added with good stirring. After stirring for 10 minutes, a small amount of urea was added to the resulting pink solution. The reaction mixture was heated up to 30° C. for 10 minutes. The dark solution was cooled to room temperature and saturated with sodium chloride. After standing overnight, the mixture was filtered and the filtrate was extracted eight times with diethyl ether (50 mL). The ether extracts were combined and concentrated under reduced pressure. The product was isolated from the residue by preparative thin layer chromatography (15% ethyl acetate in hexanes) as yellow solids (64 mg, 13%). mp 131.3° C.; IR (KBr) 1733 (C=O), 3267 (OH) cm$^{-1}$; 1H NMR (200 MHz, acetone-d6) 3.78 (s, 2H), 7.10 (d d, 1H), 7.77 (d d, 1H), 7.46 (d d, 1H), 8.84 (s, 1H, OH); MS (EI, m/e, relative intensity %) 134 (M+., 65), 106 (M+. −CO, 100). DSC showed a melting endotherm peaked at 131.3° C. and an exotherm beginning at 201.4° C. in the first scan. The second scan displayed no peaks up to 350° C.

Example 18

5-Iodobenzocyclobutenone (17)

At 0°–5° C., a solution of sodium nitrite (0.759 g) in water (5 mL) was added into a suspension of the amine 8 in 2.5 mL of concentrated sulfuric acid and 10 mL of water. After stirring for 15 minutes, a solution of potassium iodide (1.826 g) in 3 mL of water was added slowly. The cloudy, orange-purple solution was stirred at room temperature for 1 hour. The reaction mixture was diluted with water (50 mL) and extracted with with ether (2×100 mL). The etheral extracts were washed with aqueous sodium carbonate solution and water. Removal of solvent and flash chromatography of the residue afforded the iodide 17. 1H NMR (200 MHz, CDCl3) 4.00 (s, 2H), 7.27 (d d, 1H), 7.48 (d d, 1H), 8.13 (s, 1H); MS (EI, m/e, relative intensity %) 244 (M+., 12), 216 (M+. −CO, 7.8), 89 (216 (M+. −CO −.I, 40).

Example 19

Compound 18 from Reaction of 8 with Maleic Anhydride

To a solution of maleic anhydride (206 mg, 2.1 mmol) in dry diethyl ether (5 mL), was added the solid 8 (266 mg, 2.0 mmol) in one portion at room temperature. The white solids were formed immediately after addition. After 10–15 minutes, the amic acid (407 mg, 86%) was collected by filtration and dried in air. To a solution of the above amic acid in acetic anhydride (3 mL), was added dry sodium acetate (82 mg, 1.0 mmol). The mixture was heated at 80°–90° C. for 2 hours. The reaction mixture was then cooled to room temperature and poured into water (20 mL) with stirring. The mixture was then stirred until the solids were formed. The crude imide product was collected on the filter funnel, washed with water several times and dried in air. Recrystallization from toluene gave 18 as colorless crystalline solids: 222 mg (52%); mp 148°–149° C.; IR (KBr) 1711, 1763, 3084 cm$^{-1}$; 1H NMR (200 MHz, CDCl3) 4.03 (s, 2H), 6.90 (s, 2H), 7.36 (s, 1H), 7.52 (d d, 1H), 7.65 (d, 1H); MS (EI, m/e, relative intensity %) 213 (M+., 68.6), 185 (M+. −CO, 100). DSC showed a melting endotherm peaked at 146.5° C. and an exotherm beginning at 158° C. in the first scan. The second scan displayed no peaks up to 330° C.

Example 20

Compound 19 from Reaction of 8 with Methacryloyl Chloride

To a solution of 8 (230 mg, 2.2 mmol) in dry pyridine (3 mL) at room temperature, was added methacryloyl chloride (266 mg, 2.0 mmol) under nitrogen. The resulting yellow-orange solution was stirred at room temperature for 3 hours. The reaction solution was diluted with diethyl ether (50 mL) and washed with diluted hydrochloric acid three times. Removal of the solvent and subsequent recrystallization of the residue ethanol/cyclohexane afforded the pure amide product 19 as yellow crystalline flakes: 0.35 g (87%); mp 149°–150° C.; IR (KBr) 1666, 1745, 2923, 3357 cm$^{-1}$; 1H NMR (200 MHz, CDCl3). 2.27 (s, 3H), 4.13 (s, 2H), 5.69 (m, 1H), 6.01 (s, 1H), 7.45 (d, 1H), 7.70 (d, 1H), 7.79 (s, 1H), 7.87 (d d, 1H); MS (EI, m/e, relative intensity %) 201 (M+., 37.5), 173 (M+. −CO, 43.5). DSC showed a melting endotherm peaked at 147° C. and an exotherm beginning at 199° C. in the first scan. The second scan displayed no peaks up to 330° C.

Example 21

3-Nitrobenzocyclobutenone(20)

Benzocyclobutenone (1.20 g) was added slowly to concentrated sulfuric acid (5 mL) at 0° C. with vigorous stirring. The mixture of concentrated sulfuric acid (1.0 mL) and nitric acid (70%, 1.05 g) was added at such a rate that the solution temperature remained at 10° C. After the completion of addition of nitrating solution, the reaction mixture was then poured into icey water (30 mL). The resulting mixture was filtered. The filtrate was neutralized with sodium carbonate powders and the water was then evaporated under vacuum. The residue was then extracted with methylene chloride (3×50 mL). After removal of methylene chloride, the pure product (3-nitrobenzocyclobutenone) was isolated from the residue by chromatography on silica gel: 55 mg; IR (KBr) 1349, 1525, 1772 cm$^{-1}$; $^1$H NMR (200 MHz, CDCl3) 4.42 (s, 2H), 7.68 (m, 2H), 8.31 (m, 1H); MS (EI, m/e, relative intensity %) 164 (M+. +H, 2.5), 135 (M+. −CO, 10.3), 89 (135 −.NO$_2$, 38).

References

[1] R. A. Kirchhoff, U.S. Pat. No. 4,540,763 (1985).

[2] L. S. Tan and F. E. Arnold, U.S. Pat. No. 4,711,964 (1987).

[3] see leading reviews: (a) R. A. Kirchhoff, C. J. Carriere, K. J. Bruza, N. G. Rondan, and R. L. Sammler, J. Macromol. Sci. Chem., A28 (11 & 12), 1079 (1991). (b) L.-S. Tan and F. E. Arnold, J. Polym. Sci. Part A: Polym. Chem. 26, 1819 (1988). (c) R. A. Kirchhoff and K. J. Bruza, Chemtech, Sep. 22 (1993).

[4] (a) T. Endo, T. Koizumi, T. Takata, and K. Chino, J. Polym. Sci. Part A: Polym. Chem. 33, 707 (1995). (b) S. L. DeLassus, B. A. Howell, C. J. Cummings, V. A. Dais, R. M. Nelson, and D. B. Priddy, Macromolecules, 27, 1307 (1994).

[5] (a) J. Spangler and J. H. Kim, Tetrahedron Lett., 11, 1249 (1972). (b) E. Hedaya and M. E. Kent, J. Am. Chem. Soc. 92, 2149 (1970). (c) L. S. Liebeskind and M. S. South, J. Org. Chem. 47, 3815 (1982).

[6] (a) P. Schiess and M. Heitzmann, Angew. Chem. Int. Ed. Engl. 16, 469 (1977). (b) H. Hart and J. A. Hartlage, J. Am. Chem. Soc. 89, 6672 (1967). (c) K. Krohn, H. Rieger, E. Broser, P. Shiess, S. Chen, and T. Strubin, Liebigs Ann. Chem. 943 (1988). (d) P. Schiess, M. Eberle, M. Huys-Francotte, and J. Wirz, Tetrahedron Lett. 25, 2201 (1984).

[7] S. V. Kessar, P. Singh, D. Venugopal, J. Chem. Soc. Chem. Commun. 1258 (1958).

[8] Wulfman, in "The Chemistry of Diazonium and Diazo Groups", Part 1; Ed., Patai, Wiley: New York, 1978, pp. 286–297.

I claim:
1. A functionalized benzocyclobutenone of structural formula I
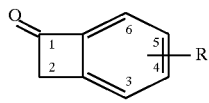
wherein R is NH₂, NO₂, N
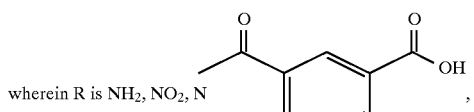
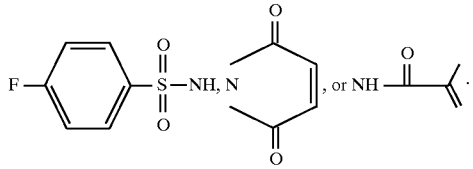
, and wherein R is at the 5- or 3-position.
2. A compound according to claim 1, wherein R is NH₂ or NO₂.
3. A compound according to claim 1, wherein R is at the 5- or 3-position on the benzene ring.
4. A compound according to claim 1, of structural formula
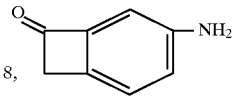
* * * * *